United States Patent
Barbera et al.

(10) Patent No.: US 10,329,253 B2
(45) Date of Patent: Jun. 25, 2019

(54) PROCESS FOR THE SYNTHESIS OF 2-(2,5-DIMETHYL-1H-PYRROL-1-YL)-1,3-PROPANEDIOL AND ITS SUBSTITUTED DERIVATIVES

(71) Applicant: Politecnico di Milano, Milan (IT)

(72) Inventors: Vincenzina Barbera, Biancavilla (IT); Attilio Citterio, Milan (IT); Maurizio Stefano Galimberti, Milan (IT); Gabriella Leonardi, Milan (IT); Roberto Sebastiano, Lazzate (IT); Suresh Udhavrao Shisodia, Parbhani (IN); Antonio Marco Valerio, Sesto S. Giovanni (IT)

(73) Assignee: Politencnico di Milano, Milan (IT)

( * ) Notice: Subject to any disclaimer, the term of this patent is extended or adjusted under 35 U.S.C. 154(b) by 64 days.

(21) Appl. No.: 15/318,300

(22) PCT Filed: Jun. 12, 2015

(86) PCT No.: PCT/EP2015/063221
§ 371 (c)(1),
(2) Date: Dec. 12, 2016

(87) PCT Pub. No.: WO2015/189411
PCT Pub. Date: Dec. 17, 2015

(65) Prior Publication Data
US 2017/0101376 A1      Apr. 13, 2017

(30) Foreign Application Priority Data
Jun. 13, 2014   (IT) ................... MI2014A1077

(51) Int. Cl.
*C07D 207/333*   (2006.01)
*C07D 498/16*    (2006.01)

(52) U.S. Cl.
CPC ....... *C07D 207/333* (2013.01); *C07D 498/16* (2013.01)

(58) Field of Classification Search
None
See application file for complete search history.

(56) References Cited

PUBLICATIONS

Thomas et al. Journal of Material Chemistry, 2008, 18, 4893-4908. (Year: 2008).*
Galimberti et al Polymer 63 (2015) 62-70. (Year: 2015).*
Broadbent, H., et al., "Novel Heterotricyclic Systems: 2,6-Dioxa- and 2-0xa-6-thia-10-azatricyelo- [5.2.1.0 4, 1 0] decanes; 2,6-Dioxa-11-azatricyclo [5.3.1.0 4,1 1] undecane: and 9,13-Dioxa-14-azatetracyclo [6.5.1.0 2,7 .0 1 1, 1 4] tetradeca-2,4,6-triene (1a, b)", Journal of Heterocyclic Chemistry, Wiley-Blackwell Publishing, Inc., US, (Apr. 1, 1976), vol. 13, pp. 337-348, XP002078169, ISSN: 0022-152X.
Shallu, A., et al., "Paal-Knorr Pyrrole Synthesis Using Recylable Amberlite IR 120 Acidic Resin: A Green Approach", Synthetic Communications, vol. 42: 1480-1488 (2012), ISSN: 0039-7911.
Burnham, W., et al., "Synthesis via Modifications of the Knorr-Paal Procedure: A. Derivatives of 2,6-Dioxa-10-Azatricyclo [5.2.1.0(4, 10)] Decane. B. Highly Sterically Crowded 1, 2, 5-Trialkylpyrroles and Pyrrolidines", Dissertation Abstracts B, vol. 29, No. 11, Jan. 1, 1969 (Jan. 1, 1969), pp. 4088-B-4099-B, XP009181054, ISSN: 0420-073X; & Database Registry [online], Chemical Abstracts Service, Columbus, Ohio, US; Nov. 16, 1984 (Nov. 16, 1984); Database accession No. 33082-27-8.

* cited by examiner

*Primary Examiner* — Nyeemah A Grazier
(74) *Attorney, Agent, or Firm* — Margaret Millikin

(57) ABSTRACT

The present invention relates to a process for the synthesis of molecules that have a pyrrole ring bonded to a diol. In particular, the invention relates to the synthesis of molecules that have the pyrrole ring and a diol derived from serinol by means of a process that does not demand the use of solvents or chemical catalysts.
The process consists of a first reaction phase that takes place without any solvents and/or organic diluents, giving rise to an intermediate compound, and a second phase in which the intermediate compound is converted into the required compound by heating the reaction mixture to a temperature ranging from 100° to 200° C. for an interval in the range of 1 to 500 minutes, or by adding a carbon allotrope or its derivatives.

8 Claims, No Drawings

PROCESS FOR THE SYNTHESIS OF 2-(2,5-DIMETHYL-1H-PYRROL-1-YL)-1,3-PROPANEDIOL AND ITS SUBSTITUTED DERIVATIVES

CROSS-REFERENCE TO RELATED APPLICATIONS

This application is a continuation and national stage application of International Application No. PCT/EP2015/063221, filed Jun. 12, 2015, which claims the benefit of Italian Patent Application No. MI2014A001077 filed on Jun. 13, 2014, the entire contents of both of which are hereby incorporated by reference.

The present invention relates to a process for the synthesis of molecules that have a pyrrole ring bonded to a diol.

In particular, the invention concerns the synthesis of molecules that have the pyrrole ring and a diol derived from serinol by means of a process that does not involve the use of solvents or chemical catalysts, and that consequently has a minimal environmental impact, generating no polluting waste products. The invention particularly relates to the synthesis of 2-(2,5-dimethyl-1H-pyrrol-1-yl)-1,3-propanediol (hereinafter called serinol pyrrole) and its substituted derivatives.

Serinol derivatives containing a pyrrole ring, and serinol pyrrole and its substituted derivatives in particular, can be important reaction intermediates in organic synthesis, and "building blocks" for the preparation of supramolecular structures. They are capable of giving rise to reactions with various chemical species, and non-bonded interactions.

In particular, the aromatic ring is capable of interacting with other aromatic molecules, and with hydrocarbon substances, and it can serve as a substrate for the chemical reactions typical of said aromatic substances.

The hydroxyl groups of pyrrole can interact with polar molecules and also generate a great variety of modifications in the original molecule through reactions with functional groups such as isocyanates, acids, anhydrides, halides, and others.

Changes in the chemical nature of serinol pyrrole induced by inserting substitutes on the aromatic chain in positions alpha and beta, and/or substitutes on the alkyl chains carrying the hydroxyl groups, lead to modifications of the properties of serinol pyrrole, such as its solubility in various solvents, and its compatibility with polymer matrices.

Pyrroles also constitute a class of heterocyclic compounds with different types of biological activity. Some compounds in this class are used for their antimalarial, anti-inflammatory, anti-asthma, bactericidal, and antihypertensive effects, and also as tyrosine kinase inhibitors. Molecules containing the pyrrole ring are widespread in nature too, e.g. vitamin B12, and porphyrins. These molecules, as such or modified, are prepared synthetically for a variety of uses.

Thus, given the importance of pyrroles and their derivatives in various applications, it is essential to have an effective and industrially advantageous method for their synthesis. Numerous contributions in the literature describe the synthesis of pyrroles, and of serinol pyrrole in particular. For instance, the article entitled "*Paal-Knorr pyrrole synthesis using recyclable amberlite ir 120 acid resin*" by Aarti Devi et al. (Synthetic Communication, 42: 1480-1488, 2012) describes a process for the synthesis of pyrroles in which an acid resin of amberlite ir 120 is used as a catalyst. Although this process assures a high pyrrole yield, it has an important drawback relating to the presence of the catalyst, which has to be removed from the compound by means of subsequent purifying and distilling steps in order to avoid impurities in the compound making it unsuitable for use, especially in the pharmaceutical sector.

The article entitled "*Novel heterotricyclic system: 2,6-dioxa- and 2-oxa-6-thia-10-azatricyclo[5.2.1.04,10] decanes . . .*" by H. Smith Broadbent et al. (Journal of Heterocyclic Chemistry, 1976, volume 13, issue 2, pages 337-348) describes a process for the synthesis of serinol pyrrole or its derivatives substituted in position alpha, in which a diketone is reacted with serinol using solvents such as toluene or heptane, and acid catalysts to facilitate the reaction. This process has the drawback, however, of giving rise to a mixture of products in which serinol pyrrole is contained in small quantities. It is a process characterized by a poor selectivity. In addition, the serinol pyrrole is diluted in organic solvents that have to be removed, and that pollute the environment and harm human health.

It is common general knowledge that the solvents have a significant effect on the performance of chemical reactions.

Solvents are involved in the following main aspects of chemical reactions: solubility of reagents, reactivity, rate constant and equilibrium constant and thermal balance of the reaction.

The importance of solvents to solubilise the reagents is clearly reported in a journal dedicated to drugs. In Marvanya, 2011 (Hiren M. Marvaniya, Kaumil N. Modi and Dhrubo Jyoti Sen, International Journal of Drug Development & Research. April-June 2011, Vol. 3, Issue 2, ISSN 0975-9344) it is written: "A general assumption with regard to organic reactions is that they are performed in a solvent medium. The rationale behind this concept is simple. That is, the reactants can interact effectively if they are in a homogeneous solution, which facilitates the stirring, shaking or other ways of agitation, whereby the reactant molecules come together rapidly and continuously".

In (Marvanya, 2011) is also written "Changing of solvent of a reaction can influence the rate of that reaction and it can be powerful enough to change the reaction course itself. This may manifest in altered yields and ratios of the products. Thus a solvent could be deeply and inseparably associated with the process of an organic reaction through the solvation of the reactants".

In Schmid, 2001 (Roland Schmid, "Effect of Solvent on Chemical Reactions and Reactivity" Page 737-13.1-Solvent Effects On Chemical Reactivity-) it is written that "It can be said without much exaggeration that studying solvent effects is one of the most central topics of chemistry and remains ever-increasingly active".

Moreover, the effect of solvent on chemical reactions is absolutely relevant, regardless of the nature of the solvent. In (Schmid, 2001), it is also written: "Traditionally, it is held that solvent structure only assumes importance when highly structured solvents, such as water, are involved. But this view increasingly turns out to be erroneous. In fact, ignoring solvent-solvent effects, even in aprotic solvents, can lead to wrong conclusions".

On the basis of what written above, solvents have dramatic effects on chemical reactions, and it is not possible a reasonable forecast on the effect of the removal of solvents in the reactions. Therefore it is clear that removal of solvent(s) can have dramatic effect on chemical reactions. Hence it would be desirable to devise a process for the synthesis of serinol pyrrole and its substituted derivatives than can be completed without the aid of organic solvents that may be toxic for humans and damage the environment. It would likewise be desirable to avoid the formation of waste products that demand treatment and disposal in order to protect the environment and prevent their polluting effects. It would also be desirable to devise a process for the synthesis of serinol pyrrole and its substituted derivatives that affords a high yield of end product, and gives rise to a product of high purity that needs no further distillation or separation from unreacted reagents or reaction catalysts that might make the final compound unsuitable for its intended purpose. Finally, it would be desirable to devise a synthesis process with an energy demand such that it enables a high product yield with a minimal energy consumption, and a consequently low cost.

One object of the present invention is therefore a process for the synthesis of serinol pyrrole capable of delivering serinol pyrrole in pure form, with no need for any further phases of purification and separation from the byproducts.

Another object of the present invention is a process for the synthesis of serinol pyrrole and its substituted derivatives capable of functioning without the aid of organic solvents, and consequently without any waste products requiring treatment or disposal, so that the result is a process that safeguards the environment and human health.

Another object of the present invention is a synthesis process that is easy to implement with a limited energy consumption and low operating costs.

These and other objects of the present invention are achieved by means of a process for the preparation of a compound of formula (I)

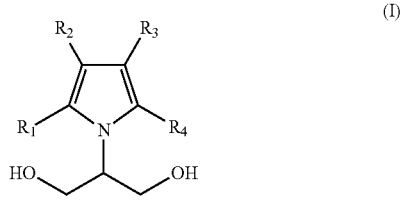

wherein $R_1$, $R_2$, $R_3$, $R_4$ are independently selected from the group consisting of: hydrogen, $C_1$-$C_{30}$ alkyl, $C_2$-$C_{30}$ alkenyl, $C_2$-$C_{30}$ alkynyl, $C_2$-$C_{30}$ linear or branched alkyl, aryl, alkyl-aryl, $C_2$-$C_{30}$ linear or branched alkenyl-aryl, $C_2$-$C_{30}$-alkynyl aryl, heterocycle, said process comprising the following phases:

a) reacting a compound of formula (II)

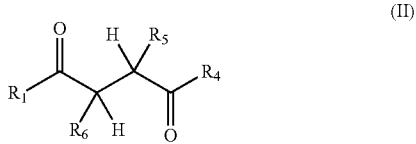

wherein $R_1$, $R_4$ are independently selected from the group consisting of: hydrogen, $C_1$-$C_{30}$ alkyl, $C_2$-$C_{30}$ alkenyl, $C_2$-$C_{30}$ alkynyl, $C_2$-$C_{30}$ linear or branched alkyl, aryl, alkyl-aryl, $C_2$-$C_{30}$ linear or branched alkenyl-aryl, $C_2$-$C_{30}$-alkynyl aryl, heterocycle, and $R_5$, $R_6$ are independently selected from the group consisting of: hydrogen, $C_1$-$C_{30}$ alkyl, $C_2$-$C_{30}$ alkenyl, $C_2$-$C_{30}$ alkynyl, $C_2$-$C_{30}$ linear or branched alkyl, aryl, alkyl-aryl, $C_2$-$C_{30}$ linear or branched alkenyl-aryl, $C_2$-$C_{30}$-alkynyl aryl, heterocycle, with a compound of formula (III)

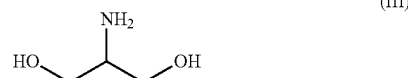

without any solvents and/or organic diluents, thereby obtaining an intermediate compound of formula (IV)

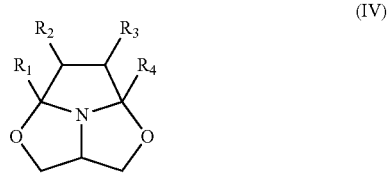

wherein $R_1$, $R_2$, $R_3$, $R_4$ are independently selected from the group consisting of: hydrogen, $C_1$-$C_{30}$ alkyl, $C_2$-$C_{30}$ alkenyl, $C_2$-$C_{30}$ alkynyl, $C_2$-$C_{30}$ linear or branched alkyl, aryl, alkyl-aryl, $C_2$-$C_{30}$ linear or branched alkenyl-aryl, $C_2$-$C_{30}$-alkynyl aryl, heterocycle;

b) converting the compound of formula (IV) into the compound of formula (I) by heating the reaction mixture to a temperature in the range of 100° to 200° C. for a time ranging from 1 to 500 minutes, or by adding a carbon allotrope or its derivatives.

This gives rise to a compound like serinol pyrrole or its substituted derivatives by means of a simple reaction without any byproducts.

In the process according to the present invention, it is preferable for phase (a) reacting the compound of formula (II) with the compound of formula (III) to be completed without any acids.

This gives rise to a compound with a high grade of purity that needs no further purification steps to remove acid residues that may influence the future uses of said compound.

In the process according to the present invention, said $R_1$, $R_2$, $R_3$, and $R_4$ are preferably independently selected from the group consisting of: hydrogen, $C_1$-$C_{18}$ alkyl, $C_2$-$C_{18}$ alkenyl, $C_2$-$C_{18}$ alkynyl, $C_2$-$C_{18}$ linear or branched alkyl, aryl, alkyl-aryl, $C_2$-$C_{18}$ linear or branched alkenyl-aryl, $C_2$-$C_{18}$ alkynyl aryl, heterocycle, and said $R_5$, $R_6$ are preferably independently selected from the group consisting of: hydrogen, $C_1$-$C_{18}$ alkyl, $C_2$-$C_{18}$ alkenyl, $C_2$-$C_{18}$ alkynyl, $C_2$-$C_{18}$ linear or branched alkyl, aryl, alkyl-aryl, $C_2$-$C_{18}$ linear or branched alkenyl-aryl, $C_2$-$C_{18}$ alkynyl aryl, heterocycle.

In the process according to the present invention, R1, R2, R3, and R4 are more preferably selected from the group consisting of: H, $CH_3$, $CH_2CH_3$, phenyl, and said $R_5$, $R_6$ are more preferably independently selected from the group consisting of: H, $CH_3$, $CH_2CH_3$.

In the process according to the present invention, the carbon allotrope is preferably selected from the group comprising: carbon black, fullerene, single-wall or multiwall carbon nanotubes, graphene, graphite with a number of graphene layers in a range of 2 to 10000.

In the process according to the present invention, the carbon allotrope derivative to which reference is made preferably contains functional groups selected from the group comprising:

oxygenated functional groups, and preferably hydroxyls, epoxides;

functional groups containing carbonyls, and preferably aldehydes, ketones, carboxylic acids;

functional groups containing nitrogen atoms, and preferably amines, amides, nitriles, diazonium salts, imines;

functional groups containing sulfur atoms, and preferably sulfides, disulfides, mercaptans, sulfones, sulfinic and sulfonic groups.

It is consequently possible to choose from a broad variety of substrates that can also function as catalysts, and that enable the required compound to be obtained rapidly and effectively.

In the process according to the invention, the carbon allotrope derivative is preferably graphite oxide (GO).

In the process according to the invention, the carbon allotrope derivative is preferably graphene oxide.

The temperature for heating the reaction mixture containing the compound (II) and the compound (III) to obtain the compound (I) according to the present invention is preferably in the range of 120° to 160° C., and said time is preferably between 30 and 80 minutes. This optimizes the yield of end product while reducing the energy consumption for the reaction.

Another object of the present invention is to obtain a stable reaction intermediate that is easy to prepare, such that it can advantageously be preserved and stored without difficulty before completing the preparation process.

This object is achieved by means of a compound of formula (IV)

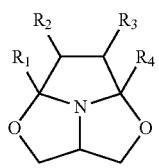
(IV)

wherein $R_1$, $R_2$, $R_3$, $R_4$ are independently selected from the group consisting of: hydrogen, $C_1$-$C_{30}$ alkyl, $C_2$-$C_{30}$ alkeny, $C_2$-$C_{30}$ alkynyl, $C_2$-$C_{30}$ linear or branched alkyl, aryl, alkyl-aryl, $C_2$-$C_{30}$ linear or branched alkenyl-aryl, $C_2$-$C_{30}$-alkynyl aryl, heterocycle, obtained by reacting a compound of formula (II)

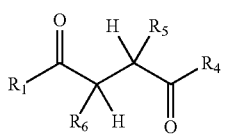
(II)

wherein $R_1$, $R_4$ are independently selected from the group consisting of: hydrogen, $C_1$-$C_{30}$ alkyl, $C_2$-$C_{30}$ alkenyl, $C_2$-$C_{30}$ alkynyl, $C_2$-$C_{30}$ linear or branched alkyl, aryl, alkyl-aryl, $C_2$-$C_{30}$ linear or branched alkenyl-aryl, $C_2$-$C_{30}$-alkynyl aryl, heterocycle, and $R_5$, $R_6$ are independently selected from the group consisting of: hydrogen, $C_1$-$C_{30}$ alkyl or, $C_2$-$C_{30}$ alkenyl, $C_2$-$C_{30}$ alkynyl, $C_2$-$C_{30}$ linear or branched alkyl, aryl, alkyl-aryl, $C_2$-$C_{30}$ linear or branched alkenyl-aryl, $C_2$-$C_{30}$-alkynyl aryl, heterocycle, with a compound of formula (III)

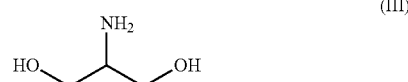
(III)

without any solvents and/or diluents and/or acids.

This gives rise to a compound that can be described as a stable reaction intermediate that is easy to store, so that the phase in which said compound is converted into the compound of formula I can be completed at any time.

The process for the preparation according to the present invention of a compound of formula (I)

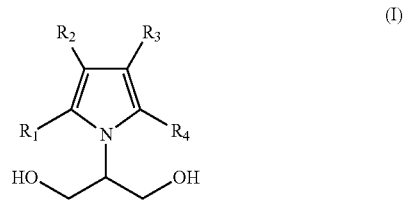
(I)

as defined above comprises a first phase (a) in which a compound of formula (II), or protected forms thereof (IIa), such as acetals, ketals, imines, hemiketals, hemiacetals, enol ethers,

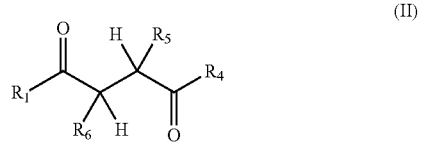
(II)

as defined above, e.g. a dialdehyde or a diketone, is placed in contact and reacted with a compound of formula (III)

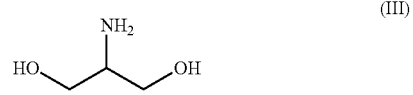
(III)

i.e. a compound comprising an amine group bonded to two hydroxyl groups, such as serinol.

The two components (I) and (II) are placed in contact and reacted with no solvents or diluents, or chemical substances such as acids, simply by physically mixing the two components at room temperature.

According to the present invention, the term acid is used to mean a substance capable of releasing protons, i.e. H$^+$ ions, to a substance capable of receiving them, defined as a base.

According to the present invention, the term acid is used to mean a Broensted-Lowry acid.

The compounds (II) and (III) are placed in contact at room temperature, in equimolar quantities.

The reaction takes place simply by mixing (II) and (III) at a rate in the range of 10 to 1500 rpm and for a time ranging between 30 and 600 minutes.

The reaction of the compound of formula (II) with the compound of formula (III) gives rise to the formation of a reaction intermediate of formula (IV)

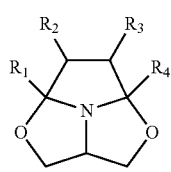

as defined above, i.e. a compound with three condensed cycles that is very stable at room temperature.

Thanks to its stability, the compound of formula (IV) can advantageously be preserved for variable periods of time, thus enabling the completion of the reaction to be postponed.

After the first phase (a), in which the reaction of the compound of formula (II) with the compound of formula (III) has led to the formation of the compound of formula (IV), the second phase (b) involves heating the reaction mixture containing the compound (IV) to a temperature ranging from 100° to 200° C. for a period of time ranging from 1 to 500 minutes to enable two of the three rings comprising the tricyclic compound of formula (IV) to be opened, thereby obtaining the compound of formula (I). The reaction is preferably conducted at a temperature in the range of 120° to 160° C. so as to increase the yield of the reaction and obtain a product of greater purity.

The pressure at which the conversion reaction is completed is preferably in the range of 1 to 12 atm, depending on the temperature to which the reaction mixture is heated.

Phase b) of the process according to the present invention can optionally be completed with a carbon allotrope or its derivative, without heating the reaction mixture.

The carbon allotrope or its derivative is used in proportions in the range of 1:1 to 10:1 with the compound (I) to be synthesized, i.e. the serinol pyrrole or one of its substituted derivatives, in a straightforward manner without any further steps or reaction phases. The reagents are added to the carbon allotrope without using any solvents. Alternatively, a suspension containing the carbon allotrope can be prepared, adding the reagents and an environment-friendly solvent, such as water, ethanol, isopropanol, acetone or ethyl acetate. The solvent is removed under reduced pressure.

The carbon allotrope is selected from the group comprising: carbon black, fullerene, single-wall or multiwall carbon nanotubes, graphene, graphite with a number of graphene layers in the range of 2 to 10000. Single-wall carbon nanotubes (SWCNT) have a mean diameter of 2 nm and are between 20 nm and 10 micron long. Multiwall carbon nanotubes (MWCNT) have a mean diameter in the range of 3 to 20 nm, and are between 20 nm and 10 micron long, with a number of walls ranging from 2 to 20.

In the process according to the present invention, the carbon allotrope derivatives taken for reference are preferably such allotropes containing functional groups as those listed below:
- oxygenated functional groups, e.g. hydroxyls, epoxides, groups containing carbonyls, such as anhydrides, aldehydes, ketones, carboxylic acids;
- functional groups containing nitrogen atoms, e.g. amines, amides, nitriles, imines;
- functional groups containing sulfur atoms, e.g. sulfides, disulfides, mercaptans, sulfones, sulfinic and sulfonic groups.

Graphite oxide is a particular example of a carbon allotrope derivative: graphite oxide (GO) is a stratified material that can be obtained by chemical oxidation of graphite. GO can be prepared by treating graphite with strong mineral acids and oxidizing agents, typically by means of a treatment with a mixture of sulfuric acid and nitric acid, using potassium chloride (Staudenmaier, L. Ber. Dtsch. Chem. Ges. 1898, 31, 1481-1487), or with a mixture of sodium nitrate, concentrated sulfuric acid, and potassium permanganate (Hummers, W. S.; Offeman, R. E. J. Am. Chem. Soc. 1958, 80, 1339). GO consists of oxidized sheets containing functional groups that confer surface polarity and a strongly hydrophilic property, as reported in He, H.; Klinowski, J.; Forster, M.; Lerf A. Chem. Phys. Lett. 1998, 287, 53-56. These functional groups include, for instance, hydroxyls, epoxides, carbonyls.

When a carbon allotrope or its derivative is used in the synthesis reaction that gives rise to the compound (I), said compound (I) forms a stable adduct with the carbon allotrope or its derivative. Particular functionalizations of the allotropes can thus be obtained, conferred by the serinol pyrrole or by its substituted derivatives, that enable a more versatile use of the so-called carbon black.

The compound of formula (I) obtained according to the above-described process can subsequently be purified to remove the unreacted reagents from the reaction mixture using typical separation methods such as distilling or chromatography. Distilling can be done under atmospheric or reduced pressure, and using not particularly high temperatures. Column chromatography can be done using silica as the stationary phase and an organic solvent or mixture of solvents as the mobile phase.

The process according to the present invention is further illustrated by means of the examples given below, which describe the operating stages in the process.

EXAMPLES

In examples 1-5, the tricyclic intermediate compound of formula (IV) is not separated but converted directly into the end product of formula (I) by means of heating.

Examples 1-3

Synthesis of 2-(2,5-dimethyl-1-pyrrolyl)-1,3-propanediol

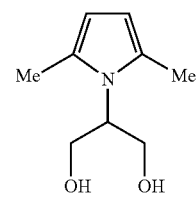 [SMILES: Cc1ccc(C)n1C(CO)CO]

Molecular weight: 169.11 a.m.u.
Physical state: viscous fluid straw yellow in colour Example 1

Place 114.1 g (1.0 mol) of 2,5-hexanedione and 91.1 g (1.0 mol) of serinol in a 250 mL single-neck flask fitted with a magnetic mixer. Leave the mixture under agitation for 6 hours at 25° C., then heat to 130° C. for 7 hours.

Distill the crude reaction product at 130° C. under reduced pressure (2 mmHg), using a glass Claisen flask connected to a mechanical vacuum pump with a plate as a heating element for the bath in which the container of crude reaction product is immersed; the product is a viscous fluid straw yellow in colour.

Example 2

Place 114.1 g (1.0 mol) of 2,5-hexanedione and 91.1 g (1.0 mol) of serinol in a 250 mL single-neck flask fitted with a magnetic mixer. Leave the mixture under agitation for 8 hours at 130° C. Distill the crude reaction product at 130° C. under reduced pressure (2 mmHg) to obtain a viscous fluid straw yellow in colour.

Example 3

Place 114.1 g (1.0 mol) of 2,5-hexanedione and 91.1 g (1.0 mol) of serinol in a 250 mL single-neck flask fitted with a magnetic mixer. Leave the mixture under agitation for 30 minutes at 150° C. Distill the crude reaction product at 130° under reduced pressure (2 mmHg) to obtain a viscous fluid straw yellow in colour.

Example 4

Synthesis of 2-pyrrol-1-yl-1,3-propanediol

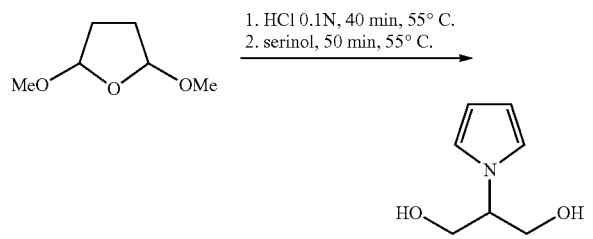

Place 1.32 g of 2,5-dimethoxytetrahydrofuran (FW: 132.16; d: 1.02 g/ml; 10 mmol), 1 g of serinol (FW: 91.11; 11 mmol) and 50 mL of HCl 0.1 N (5 mmol) under reflux in a 100 ml single-neck flask fitted with a magnetic mixer overnight. 2,5-dimethoxytetrahydrofuran is a precursor of butandial. In presence of hydrochloric acid 2,5-dimethoxytetrahydrofuran is converted in the corresponding aldehyde. Once the reaction is complete, adjust the pH of the solution to neutral by adding NaHCO$_3$ and remove the solvent from the reaction mixture with the rotavapor. Elute the residue several times with ethyl acetate to extract the reaction product, which is then purified by column chromatography using silica as the stationary phase and ethyl acetate as the mobile phase.

Example 5

Synthesis of 2-(2,5-diphenyl-1-pyrrolyl)-1,3-propanediol

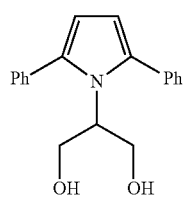 [SMILES: OCC(CO)n1c(-c2ccccc2)ccc1-c1ccccc1]

Molecular weight: 293.36 a.m.u.

Physical state: viscous fluid straw yellow in colour.

Place 2.38 g of 2,5-diphenyl-2,5-butanedione (10 mmol) and 2.73 g of serinol (30 mmol) in a 10 mL single-neck flask fitted with a magnetic mixer. Heat the mixture to 130° C. for 24 hours, then cool and elute with 20 mL of ethyl acetate, agitating the resulting heterogeneous mixture vigorously for 10 minutes. Leave to stand, then separate the overlying phase and elute the viscous residue rich in unreacted serinol with another 10 mL of ethyl acetate and repeat the previous step. Combine the extracts of ethyl acetate, remove the solvent under reduced pressure and the residue can then undergo chromatography as in Example 4, except that the eluent mixture is hexane/ethyl acetate=9/1.

Example 6

Synthesis of the Reaction Intermediate of Formula (IV), and Particularly of the Tricycle of Formula:

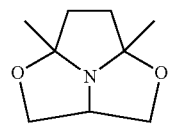

Synthesis of 4a,6a-dimethyl-hexahydro-1,4-dioxa-6b-azacyclopenta[cd]pentalene

Place 114.1 g (1.0 mol) of 2,5-hexanedione and 91.1 g (1.0 mol) of serinol in a 250 mL single-neck flask fitted with a magnetic mixer. Leave the mixture under agitation for 6 hours at 25° C., then distil at 80° C. under reduced pressure (2 mmHg), obtaining a liquid identified as 4a,6a-dimethyl-hexahydro-1,4-dioxa-6b-azacyclopenta[cd]pentalene.

Examples 7-10 below illustrate the process according to the present invention wherein the second phase (b) is completed with a catalytic system comprising carbon allotropes.

Examples 7-9 synthesis of 2-(2,5-dimethyl-1-pyrrolyl)-1,3-propanediol

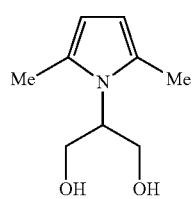

Example 7

Synthesis with Reagents Supported on MWCNT as the Carbon Allotrope

The multiwall carbon nanotubes (MWCNT) used are NC7000 series by NANOCYL™ Inc. They are used as delivered by the supplier. Place 0.200 g of MWCNT, then 0.084 g of serinol (0.922 mmol), and finally 0.105 g of 2,5-hexanedione (0.922 mmol) in a 50 mL flask at room temperature. The flask is fitted with a magnetic stirrer. Slowly rotate the mixture at a temperature of 150° C. for 120 min. Then cool the reaction mixture to room temperature. Place a sample of the solid in a test tube. Add deuterated water (D$_2$O) at room temperature. Shake the test tube manually for 2 minutes at room temperature. Filter the suspension contained in the test tube through a PTFE 0.2 micron filter. The liquid passing through the filter is colourless. This liquid can be analyzed by spectroscopy $^1$H-NMR. The compound 2-(2,5-dimethyl-1-pyrrolyl)-1,3-propanediol identified in the liquid quantitatively analyzed by spectroscopy NMR is contained in quantities of 82% mol/mol.

Example 8

Synthesis with Reagents Supported on Graphite as the Carbon Allotrope

The graphite used is Synthetic Graphite 8427, purchased from Asbury Graphite Mills Inc., with a minimum carbon content of 99.8% by weight and surface area of 330 m$^2$/g.

Place 0.200 g of graphite, then 0.084 g of serinol (0.922 mmol), and finally 0.105 g of 2,5-hexanedione (0.922 mmol) in a 50 mL flask at room temperature. The flask is fitted with a magnetic stirrer. Slowly rotate the mixture at a temperature of 150° C. for 120 minutes. Then cool the reaction mixture to room temperature. Place a sample of solid laced in a test tube. Add deuterated water (D$_2$O) at room temperature. Shake the test tube manually for 2 minutes at room temperature. Filter the suspension contained in the test tube through a PTFE 0.2 micron filter. The liquid passing through the filter is colourless. This liquid can be analyzed by spectroscopy $^1$H-NMR.

Example 9

Synthesis with Reagents Supported on Graphite Oxide

The graphite used is Synthetic Graphite 8427, purchased from Asbury Graphite Mills Inc., with a minimum carbon content of 99.8% by weight and surface area of 330 m$^2$/g.

The graphite oxide is prepared as reported in M. Galimberti, V. Cipolletti, M. Mauro, L. Conzatti, "Nanocomposites of Poly(1,4-cis-Isoprene) with Graphite Oxide Intercalation Compounds", Macromol. Chem. Phys. 214 (17) (2013) 1931-1939".

Place 0.5 g of graphite oxide, 0.500 g of serinol (0.0055 mol), 628 mg of 2,5-hexanedione (0.0055 mol), one after the other, in a 10 ml flask. Leave the mixture under agitation at room temperature for 60 minutes. Then add water (5 ml) and leave for 3 hours under agitation at room temperature. Filter the resulting mixture on silica, using ethyl acetate as eluent. Isolate the filtrate by removing the solvent under reduced pressure. The product is a viscous fluid straw yellow in colour, that can be analyzed by spectroscopy $^1$H-NMR.

Example 11 synthesis of 2-(pirrol-1-yl)-1,3-propanediol with reagents supported on graphite oxide

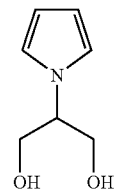

The graphite used is Synthetic Graphite 8427, purchased from Asbury Graphite Mills Inc., with a minimum carbon content of 99.8% by weight and surface area of 330 m$^2$/g.

The graphite oxide is prepared as reported in M. Galimberti, V. Cipolletti, M. Mauro, L. Conzatti, "Nanocomposites of Poly(1,4-cis-Isoprene) with Graphite Oxide Intercalation Compounds", Macromol. Chem. Phys. 214 (17) (2013) 1931-1939".

Place 0.5 g of graphite oxide, 0.500 g of serinol (0.0055 mol), 727 mg of 2,5-dimethoxytetrahydrofurane (0.0055 mol), one after the other, in a 10 ml flask at room temperature. Leave the mixture under agitation at room temperature for 60 minutes. After this interval, add 5 mL of water and leave for 3 hours under agitation. Filter the resulting mixture on silica, using ethyl acetate as eluent. Isolate the filtrate by removing the solvent under reduced pressure. The result is a viscous fluid straw yellow in colour, that can be analyzed by spectroscopy $^1$H-NMR. The spectrum recorded only identified the compound 2-(pyrrol-1-yl)-1,3-propanediol.

The invention claimed is:
1. Process for the preparation of a compound of formula (I)

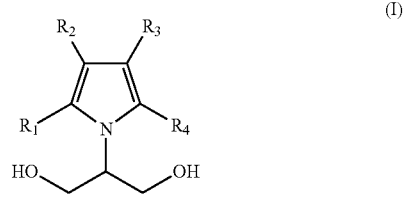

wherein R$_1$, R$_2$, R$_3$, R$_4$ are independently selected from the group consisting of: hydrogen, C$_1$-C$_{30}$ alkyl, C$_2$-C$_{30}$ alkenyl, C$_2$-C$_{30}$ alkynyl, C$_2$-C$_{30}$ linear or branched alkyl, aryl, alkyl-aryl, C$_2$-C$_{30}$ linear or branched alkenyl-aryl, C$_2$-C$_{30}$-alkynyl aryl, heterocycle, said process comprising the following steps:
a) reacting a compound of formula (II)

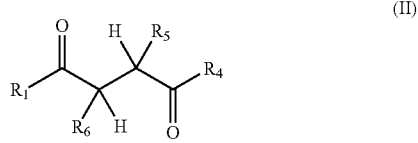

wherein R$_1$, R$_4$ are independently selected from the group consisting of: hydrogen, C$_1$-C$_{30}$ alkyl, $C_2$-$C_{30}$ alkenyl, $C_2$-$C_{30}$ alkynyl, $C_2$-$C_{30}$ linear or branched alkyl, aryl, alkyl-aryl, $C_2$-$C_{30}$ linear or branched alkenyl-aryl, $C_2$-$C_{30}$-alkynyl aryl, heterocycle, and $R_5$, $R_6$ are independently selected from the group consisting of: hydrogen, $C_1$-$C_{30}$ alkyl, $C_2$-$C_{30}$ alkenyl, $C_2$-$C_{30}$ alkynyl, $C_2$-$C_{30}$ linear or branched alkyl, aryl, alkyl-aryl, $C_2$-$C_{30}$ linear or branched alkenyl-aryl, $C_2$-$C_{30}$-alkynyl aryl, heterocycle, with a compound of formula (III)

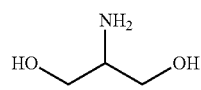

(III)

without solvents and/or organic diluents and without acids, with formation of an intermediate compound of formula (IV)

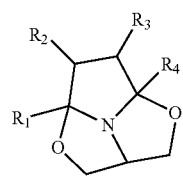

(IV)

wherein $R_1$, $R_2$, $R_3$, $R_4$ are independently selected from the group consisting of: hydrogen, $C_1$-$C_{30}$ alkyl, $C_2$-$C_{30}$ alkenyl, $C_2$-$C_{30}$ alkynyl, $C_2$-$C_{30}$ linear or branched alkyl, aryl, alkyl-aryl, $C_2$-$C_{30}$ linear or branched alkenyl-aryl, $C_2$-$C_{30}$-alkynyl aryl, heterocycle;

b) converting the compound of formula (IV) to the compound of formula (I) by heating the reaction mixture to a temperature from 100 to 200° C. for a time comprised from 1 to 500 minutes, or by adding a carbon allotrope or its derivatives.

2. Process according to claim 1, characterized in that said $R_1$, $R_2$, $R_3$, and $R_4$ are independently selected from the group consisting of: hydrogen, $C_1$-$C_{18}$ alkyl, $C_2$-$C_{18}$ alkenyl, $C_2$-$C_{18}$ alkynyl, $C_2$-$C_{18}$ linear or branched alkyl, aryl, alkyl-aryl, $C_2$-$C_{18}$ linear or branched alkenyl-aryl, $C_2$-$C_{18}$-alkynyl aryl, heterocycle, and said $R_5$, $R_6$ are independently selected from the group consisting of: hydrogen, $C_1$-$C_{18}$ alkyl, $C_2$-$C_{18}$ alkenyl, $C_2$-$C_{18}$ alkynyl, $C_2$-$C_{18}$ linear or branched alkyl, aryl, alkyl-aryl, $C_2$-$C_{18}$ linear or branched alkenyl-aryl, $C_2$-$C_{18}$ alkynyl aryl, heterocycle.

3. Process according claim 1, characterized in that said $R_1$, $R_2$, $R_3$, and $R_4$ are more independently selected from the group consisting of: H, $CH_3$, $CH_2CH_3$, phenyl, and said $R_5$, $R_6$ are independently selected from the group consisting of: H, $CH_3$, $CH_2CH_3$.

4. Process according to claim 1, characterized in that said carbon allotrope or its derivative are selected from the group consisting of: carbon black, fullerene, single-wall or multi-wall carbon nanotube, graphene, graphite with a number of graphene layers from 2 to 10000.

5. Process according to claim 1, characterized in that said carbon allotrope derivative contains functional groups, selected from the group consisting of:
- oxygenated functional groups, hydroxyl, epoxy;
- functional groups containing carbonyl, aldehydes, ketones, carboxylic acids;
- functional groups containing nitrogen atoms, amines, amides, nitriles, diazonium salts, imines;
- functional groups containing sulfur atoms, sulfides, disulfides, mercaptans, sulfones, and sulfonic groups.

6. Process according to claim 1, characterized in that said carbon allotrope derivative is graphite oxide (GO).

7. Process according to claim 1, characterized in that said carbon allotrope derivative is graphene oxide.

8. Process according to claim 1, characterized in that said temperature is from 120 to 160° C. and said time is from 30 to 80 minutes.

\* \* \* \* \*